United States Patent [19]

Noetzel

[11] 3,980,615

[45] Sept. 14, 1976

[54] FLAME RETARDING PLASTIC MATERIALS

[75] Inventor: Siegfried Noetzel, Kelkheim, Taunus, Germany

[73] Assignee: Hoechst Aktiengesellschaft, Frankfurt am Main, Germany

[22] Filed: Oct. 6, 1975

[21] Appl. No.: 620,142

[30] Foreign Application Priority Data
Oct. 7, 1974  Germany............................ 2447726

[52] U.S. Cl. ................. 260/45.75 R; 260/45.75 W; 260/502.4 P; 260/502.5
[51] Int. Cl.² ............................................ C08J 3/20
[58] Field of Search............. 260/45.9 NC, 502.4 P, 260/502.5, 45.75

[56] References Cited
UNITED STATES PATENTS

| | | | |
|---|---|---|---|
| 3,066,140 | 12/1962 | Speziale | 260/45.9 NC |
| 3,067,251 | 12/1962 | Rauhut et al. | 260/561 P |
| 3,270,092 | 8/1966 | Harwood | 260/502.4 P |
| 3,582,510 | 6/1971 | Cannelongo | 260/45.9 |
| 3,709,940 | 1/1973 | Flugel | 260/561 P |

OTHER PUBLICATIONS

Seriya Khimicheskaya vol. 8 pp. 1860–1862 1968.
Stabilization of Polymers and Stabilizer Processes – American Chemical Society publications, 1968, pp. 307 to 317.

Primary Examiner—V.P. Hoke
Attorney, Agent, or Firm—Curtis, Morris & Safford

[57] ABSTRACT

The specification discloses flame retarding plastic materials which contain, as the flame retarding agent, an alkali salt or a group II or III metal salt of a phosphinic, diphosphinic or tri-phosphinic acid derived from 2-alkyl-2,5-dioxo-1,2-oxophospholane and an organic monoamine or diamine or triamine, respectively.

2 Claims, No Drawings

FLAME RETARDING PLASTIC MATERIALS

The present invention relates to flame retarding plastic materials.

It is known that carbon compounds of phosphorus may influence the combustibility of polymers, and in certain cases they have a good flame retarding effect.

The difficulty of using organo-phosphorus compounds for flameproofing polymers resides in the fact that these compounds often have an insufficient stability under the manufacturing or processing conditions necessary for polymers, that they are not chemically inert in certain cases, or that they have a too high vapor pressure and thus volatilize under thermal strain put on the polymer, especially at reduced pressure.

It has now been found that salts of phosphinic acids corresponding to the following formulae I, II and III

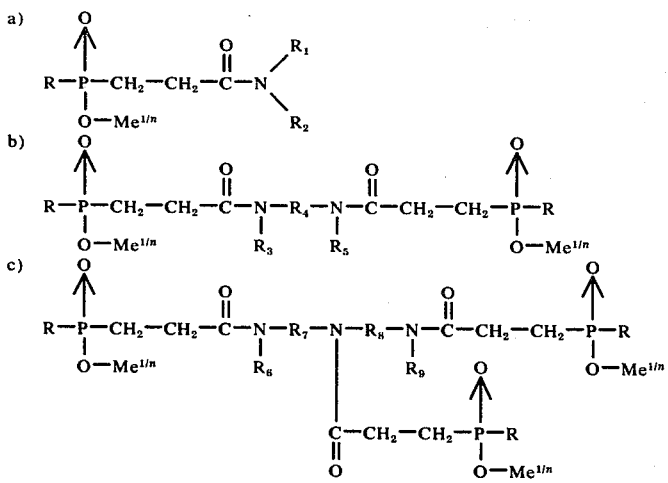

wherein
- Me is an alkali metal or a metal of the second or third main or subgroup of the Periodic System,
- $n$ indicates the valency of the metal Me,
- R is an alkyl radical having from 1 to 8 carbon atoms,
- $R_1$ is hydrogen or an open-chain or cyclic alkyl radical having from 1 to 18 carbon atoms and containing optionally halogen atoms, or an aryl or aralkyl radical optionally being substituted by halogen atoms,
- $R_2$ is an open-chain or cyclic alkyl radical having from 1 to 18 carbon atoms and containing optionally halogen atoms, or an aryl or aralkyl radical optionally being substituted by halogen atoms,
- $R_3$ is hydrogen or an open-chain or cyclic alkyl radical having from 1 to 18 carbon atoms and containing optionally halogen atoms,
- $R_4$ is an open-chain alkylene radical having from 1 to 18 carbon atoms or a cyclic alkylene, arylene, arylalkylene, arylene-alkylene or arene-bisalyklene radical having from 1 to 6 carbon atoms in the alkylene radical,
- $R_5$, $R_6$, $R_9$ are as defined for $R_3$, and $R_7$ and $R_8$ are as defined for $R_4$; the radicals $R_3$, $R_5$, $R_6$ and $R_9$ on the one hand, and $R_4$, $R_7$ and $R_8$ on the other hand being identical or different.

a very suitable flameproofing agents for polymers.

The present invention provides polymer molding compositions containing a flameproofing agent, wherein the flame-proofing agent is a phosphinic acid salt corresponding to the formulae

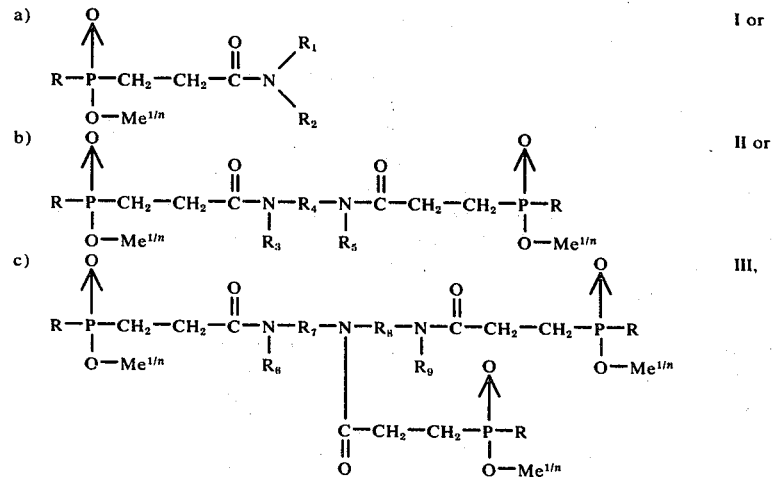

wherein Me, $n$, R, $R_1$, $R_2$, $R_3$, $R_4$, $R_5$, $R_6$, $R_7$, $R_8$ and $R_9$ are as defined above.

Examples of phosphinic acids the salts of which may be used in accordance with this invention are the following: the reaction products of a 2-alkyl-2,5-dioxo-1,2-oxaphospholane, for example of 2-methyl-2,5-dioxo-1,2-oxaphospholane, 2-ethyl-2,5-dioxo-1,2-oxaphospholane, 2-propyl-2,5-dioxo-1,2-oxaphospholane, 2-butyl-2,5-dioxo-1,2-oxaphospholane, 2-hexyl-2,5-dioxo-1,2-oxaphospholane or 2-octyl-2,5-dioxo-1,2-oxxaphospholane with a. an organic monoamine $NHR_1R_2$, for example methylamine, dimethylamine, ethylamine, diethylamine, propylamine, dipropylamine, butylamine, dibutylamine, 2,3-dibromopropylamine, bis-(2,3-dibromopropyl)-amine, octylamine, dodecylamine, stearylamine, cyclohexylamine, aniline, diphenylamine, 4-chloroaniline, 2,4,6-trichloroaniline, 4-bromoaniline, 2,4,6-tribromoaniline, or b. an organic diamine

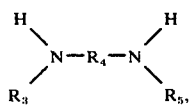

for example ethylenediamine, tetramethylenediamine, hexamethylenediamine, bisaminomethylcyclohexane, bisaminomethylnorbornane, xylylenediamine, or c. an organic triamine

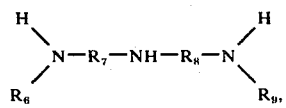

for example diethylenetriamine. The radicals $R_1$ through $R_9$ are as defined above.

The free posphinic acids are advantageously prepared as follows: equivalent amounts of the phospholane and the amine are heated to a temperature of from 80° to 220°C in the presence or absence of solvents, for example benzene, chloro- or dichlorobenzene. After complete reaction, the reaction product generally precipitates in the form of a crystalline substance which is soluble in sodium hydroxide solution.

The alkali metal salts of the phosphonic acids are obtained in the form of solid substances by dissolving crystalline phosphinic acids in the equivalent amount of the aqueous alkali metal hydroxide and subsequently concentrating them to dryness. The phosphinic acid salts of metals having higher valencies are obtained by adding aqueous solutions of salts, for example chlorides or sulfates, of the higher valency metals to the aqueous alkali metal salt solutions of the phosphinic acids, and filtering off and drying the precipitates. According to this method, for example, the calcium, magnesium, zinc or aluminum salt of the phosphinic acids may be obtained with good yields.

Especially preferred salts of the phosphinic acids are salts of the elements of the second or third group of the Periodic System, for example salts of Mg, Zn or Al.

The amount of phosphinic acid salt to be used depends on the kind of polymer and the flame retarding effect and is generally in a range of from 5 to 40, preferably 6 to 30, and especially from 8 to 25 weight %, calculated on the weight of the polymer.

Polymers which may be flameproofed by means of the phosphinic acid salts according to this invention, are polyamides, polyester amides polyurethanes, polyacetals and saturated polyesters, homo- and copolymers of olefinically unsaturated monomers, such as propylene polymers, polystyrene or styrene/acrylonitrile copolymers. Above all, the cited phosphinic acid salts may be used for flameproofing linear polyamides derived from aliphatic dicarboxylic acids having from 4 to 18 carbon atoms and aliphatic diamines having from 4 to 18 carbon atoms, and from aliphatic dicarboxylic acids having from 4 to 18 carbon atoms and/or aromatic dicarboxylic acids having from 7 to 18 carbon atoms and cycloaliphatic diamines having from 6 to 18 carbon atoms, polycaprolactam, polyalkyleneterephthalates such as polyethyleneterephthalate, polypropyleneterephthalate or polybutyleneterephthalate, polyacetals such as polyformaldehyde or trioxan copolymers or polypropylene.

A special advantage of the invention resides in the fact that the phosphinic acid salts do not adversely affect the processing of the polymers.

The incorporation of the phosphinic acid salts is advantageously carried out by blending them with polymer granules or powder and processing the blend on an injection molding machine. The polymer granules may also be premixed continuously or batchwise with the phosphinic acid salts and possible other additives, such as dyestuffs, lubricants or stabilizers, and the mixture may then be fed to an extruder for homogenization and processing to strands or ribbons. The extruded polymer melt may for example be cooled in a water bath and granulated after solidification. Halogen-free phosphinic acid salts may also be incorporated into the polymers by adding them to the starting monomer at the beginning of the polymerization process.

The flame retarding action of the phosphinic acid salts is examined according to ASTM D 635–68 on test specimens having dimensions of 127 × 12.7 × 1.6 mm. The polyamide molding compositions of the invention are either self-extinguishing or non-flammable, depending on the kind of polymer and the concentration of the flameproofing agent.

For example, a content of 15 weight % of the magnesium salt of the phosphinic acid obtained from 2-methyl-2,5-dioxo-1,2-oxaphospholane and 2,4,6-tribromoaniline in polypropylene ensures excellent flame retarding properties.

The phosphorus compounds contained in the flame retarding polymer molding compositions of the invention are thermostable and do not adversely affect the polymers neither during their preparation nor during their processing, and because of their salt character, they are non-volatile under the preparation and processing conditions.

Besides the phosphonic acid salts, there may be added to the molding compositions of the invention also inorganic fiber materials in usual amounts, for example glass fibers, or fibers of quartz, asbestos or carbon. The thickness of especially the glass fibers is advantageously in a range of from 0.1 to 50, preferably from 3 to 15, microns, and their length from 0.01 to 5, preferably from 0.05 to 1 mm. The amount of the fibers is advantageously up to 50, preferably from 10 to 30 weight %, calculated on the flame-proof molding compositions of the invention.

The polyamide molding compositions of the invention may also contain further known additives, for example stabilizers, lubricants, dyestuffs, mold release agents, antistatic or fillers.

The following examples illustrate the invention.

EXAMPLE 1a

A polyamide prepared from 1 mole of terephthalic acid, 1 mole of bisaminoethylnorbornane mixture and 25 weight % of ε-caprolactam, after grinding and screening through a sieve having a mesh size according to DIN 4188 No. 20, was homogeneously blended with 20 weight % of the sodium salt of the phosphinic acid derived from 2-methyl-2,5-dioxo-1,2-oxapholane and 2,4,6-tribromoaniline, calculated on the weight of the polyamide, and compression molded to plates having a thickness of 1.6 mm (RSV=1.13 dl/g) at 235°C and a pressure of from 5 to 100 atm/gage. From these plates, test specimens having dimensions of 127 × 12.7 × 1.6 mm were cut, which were subjected to the combustion test according to ASTM D 635–68 in order to prove the flame retarding effect. The result is indicated in Table 1.

EXAMPLE 1b (Comparative Example)

The polyamide of Example 1a, without addition of the phosphinic acid salt of Example 1a, was processed to test specimens and examinated according to ASTM D 635–68.

EXAMPLE 2a

A polyamide prepared from 1 mole of terephthalic acid, 1 mole of 1,3-bisaminomethyl-cyclohexane (substantially in trans-form) and 30 weight % of ε-caprolactam was ground, screened (see Example 1a), homogeneously blended with 15 weight %, calculated on the polyamide weight, of the sodium salt of the phosphinic acid of Example 1a, and molded as indicated in Example 1a (RSV=0.95 dl/g). The test specimens were examined according to ASTM D 635–68. The result is indicated in Table 1.

EXAMPLE 2b (Comparative Example)

The polyamide of Example 2a, without addition of the phosphinic acid salt of Example 2a, was tested according to ASTM D 635–68.

EXAMPLE 3a

Ground polyethyleneterephthalate was homogeneously blended with 10 weight % of the sodium salt of the phosphinic acid of Example 1a, calculated on the weight of the polyethyleneterephthalate, and test specimens were manufactured as indicated in Example 1a (RSV=0.82 dl/g), which specimens were examined according to ASTM D 635–68.

EXAMPLE 3b (Comparative Example)

The polyethyleneterephthalate of Example 3a, without addition of the sodium salt of the phosphinic acid of Example 3a, was tested according to ASTM D 635–68.

EXAMPLE 4a

Polypropylene powder was homogeneously blended with 20 weight % of the zinc salt of the phosphonic acid of Example 1a, calculated on the weight of the polypropylene, and plates and test specimens were manufactured as described in Example 1a (RSV=2.04 dl/g). The test specimens were examined according to ASTM D 635–68.

EXAMPLE 4b (Comparative Example)

The polypropylene of Example 4a, without addition of the zinc salt of the phosphinic acid of Example 4a, was tested according to ASTM D 635–68.

EXAMPLE 5a

A polyamide prepared from 1 mole of terephthalic acid, 1 mole of 1,3-bisaminomethyl-cyclohexane (substantially in trans-form) and 30 weight % of adipic acid-hexamethylenediamine salt was ground and screened (see Example 1a) and homogeneously blended with 30 weight %, calculated on the polyamide weight, of the zinc salt of the phosphinic acid derived from 2-methyl-2,5-dioxo-1,2-oxapholane and di-n-butylamine. As indicated in Example 1a, plates and test specimens (RSV=1.7 dl/g) were manufactured from the molding composition. The specimens were examined according to ASTM D 635–68.

EXAMPLE 5b (Comparative Example)

The polyamide of Example 5a, without addition of the phosphinic acid salt of Example 5a, was processed to test specimens and examined according to ASTM D 635–68.

The bisaminomethylnorbornane mixture used in Examples 1a and 1b was obtained according to known methods by hydroformylation of 2-cyano-bicyclo-[2,2,1-]-heptene-5 and subsequent reduction amination (reaction with ammonia and hydrogen) of the formyl compound to form the bis-(aminomethyl)-bicyclo[2,2,1]-heptane mixture.

TABLE 1

| Example | Polymer | Flame retarding agent (FRA) | weight % FRA | molded plate RSV [dl/g] | Result acc. to ASTM D 635–68 |
|---|---|---|---|---|---|
| 1a | polyamide from TA, BN and ε-caprolactam | sodium salt of the phosphinic acid from 2-methyl-2,5-dioxo-1,2-oxaphospholane and 2,4,6-tribromo-aniline | 20 | 1.13 | non-flammable |
| 1b | " | — | — | 1.25 | flammable |
| 2a | polyamide from TA, 1,3-BAC and ε-caprolactam | sodium salt of the phosphinic acid of Example 1a | 15 | 0.95 | non-flammable |
| 2b | " | — | — | 1.21 | flammable |
| 3a | polyethyleneterephthalate | sodium salt of the phosphinic acid of Example 1a | 10 | 0.82 | non-flammable |
| 3b | " | — | — | 0.86 | flammable |
| 4a | polypropylene | zinc salt of the phosphinic acid from 2-methyl- | 20 | 2.04 [1] | non-flammable |

TABLE 1-continued

| Example | Polymer | Flame retarding agent (FRA) | weight % FRA | molded plate RSV [dl/g] | Result acc. to ASTM D 635-68 |
|---|---|---|---|---|---|
| 4b | " | 2,5-dioxo-1,2-oxaphospholane and 2,4,6-tribromo-aniline | — | 2.12 [1] | flammable |
| 5a | polyamide from TA, 1,3-BAC and AH salt | zinc salt of the phosphinic acid from 2-methyl-2,5-dioxo-1,2-oxa-phospholane and di-n-butylamine | 30 | 1.07 | non-flammable |
| 5b | " | — | — | 1.13 | flammable |

TA = terephthalic acid; AH salt = adipic acid-hexamethylenediamine salt;
BN = bisaminomethylnorbornane mixture; 1,3-BAC = 1,3-bisaminomethylcyclohexane;
RSV = reduced specific viscosity measured on a solution of 1 g of the polymer in 100 ml of phenol/tetrachloroethane (60/40 weight %) at 25°C;
[1] = measured on a solution of 0.1 g of polypropylene in 100 ml of decaline at 135°C.

I claim:

1. A polymer molding composition containing a flameproofing agent, wherein the flameproofing agent is a phosphinic acid salt corresponding to the formulae

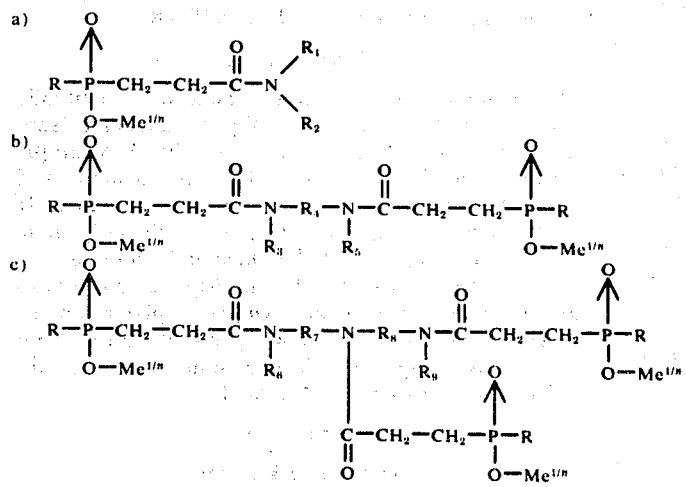

wherein
Me is an alkali metal or a metal of the second or third main or subgroup of the Periodic System,
$n$ indicates the valency of the metal Me,
R is an alkyl radical having from 1 to 8 carbon atoms, radical optionally being substituted by halogen atoms,
$R_2$ is an open-chain or cyclic alkyl radical having from 1 to 18 carbon atoms and containing optionally halogen atoms, or an aryl or aralkyl radical optionally being substituted by halogen atoms,
$R_3$ is hydrogen or an open-chain or cyclic alkyl radical having from 1 to 18 carbon atoms and containing optionally halogen atoms,
$R_1$ is hydrogen or an open-chain or cyclic alkyl radical having from 1 to 18 carbon atoms and containing optionally halogen atoms, or an aryl or aralkyl $R_4$ is an open-chain alkylene radical having from 1 to 18 carbon atoms or a cyclic alkylene, arylene, arylalkylene, arylene-alkylene or arene-bisalkylene radical having from 1 to 6 carbon atoms in the alkylene radical,
$R_5$, $R_6$, $R_9$ are as defined for $R_3$, and $R_7$ and $R_8$ are as defined for $R_4$;
the radicals $R_3$, $R_5$, $R_6$ and $R_9$ on the one hand, and $R_4$, $R_7$ and $R_8$ on the other hand being identical or different, 2. The polymer molding composition as claimed in claim 1, wherein the phosphinic acid salt is contained in an amount of from 5 to 40, preferably from 6 to 30, and especially from 8 to 25 weight %, calculated on the weight of the polymer.

* * * * *